United States Patent [19]

Vescovini

[11] Patent Number: 4,942,901

[45] Date of Patent: Jul. 24, 1990

[54] FLUID CUTOFF DEVICE IN A FLUID LINE

[76] Inventor: Pietro Vescovini, Via Artigiani, 10/12, 41056 Medolla, (Modena), Italy

[21] Appl. No.: 366,800

[22] Filed: Jun. 14, 1989

[30] Foreign Application Priority Data

Jun. 15, 1988 [IT] Italy ................. 20977 A/88

[51] Int. Cl.$^5$ ................................ F16L 37/28
[52] U.S. Cl. ..................... 137/614.06; 137/614.03; 137/614.04; 137/270; 251/149.5
[58] Field of Search ............ 137/614.03, 614.04, 137/614.06, 614.01, 270; 251/149.5, 149.9

[56] References Cited

U.S. PATENT DOCUMENTS

| 520,239 | 5/1894 | Merrick | 251/149.5 |
|---|---|---|---|
| 1,690,216 | 11/1928 | Davis | 251/149.5 |
| 1,968,075 | 7/1934 | Ewald | 251/149.5 |
| 2,044,252 | 6/1936 | Mitchell et al. | 251/149.5 |
| 2,457,251 | 12/1948 | Main, Jr. | 137/614.03 |
| 2,509,444 | 5/1950 | Mitchell | 137/614.04 |
| 3,441,055 | 4/1969 | Pickell | 137/614.06 |

FOREIGN PATENT DOCUMENTS 623926  5/1949  United Kingdom ........... 137/614.03

Primary Examiner—A. Michael Chambers
Attorney, Agent, or Firm—Peter C. Richardson; Lawrence C. Akers; Roger C. Turner

[57] ABSTRACT

A fluid cutoff device in a line, includes a first coupling having a generally cylindrically shaped outer body, and a hollow generally cylindrically shaped inner body with a first inner sealing surface. The first coupling includes a first shutter valve adapted to be normally biased closed to abut against the first sealing surface to cut off fluid flow through the first coupling. The device includes a second coupling having a generally cylindrically shaped outer body adapted to sealably translate within the inner body of said first coupling, and a hollow generally cylindrically shaped inner body with a second inner sealing surface. The second coupling includes a second shutter valve and is adapted to be normally biased closed against the second sealing surface to cut off fluid flow through the second coupling which is engagable with the second shutter valve and a second actuation means within the second coupling engagable with the first shutter valve adapted to separate the respective shutter valve from the respective sealing surface to open the couplings.

8 Claims, 4 Drawing Sheets

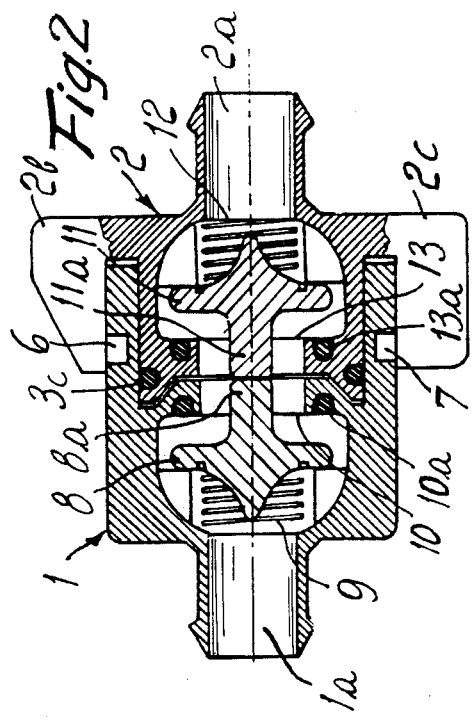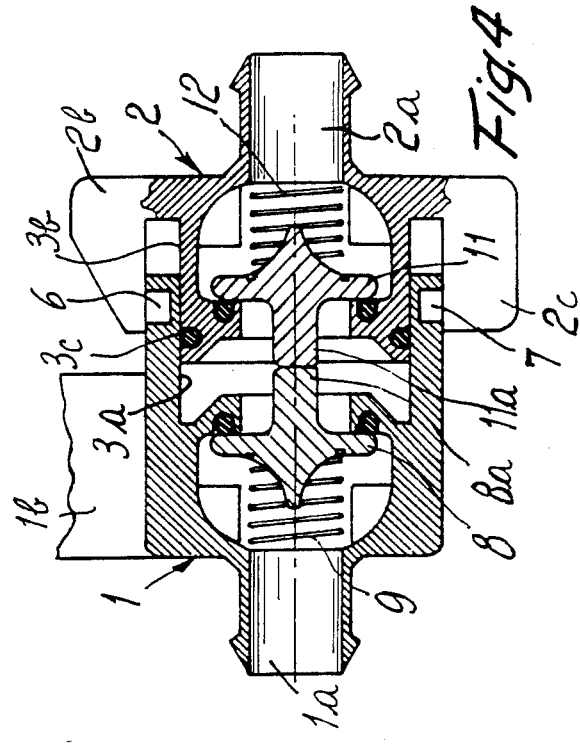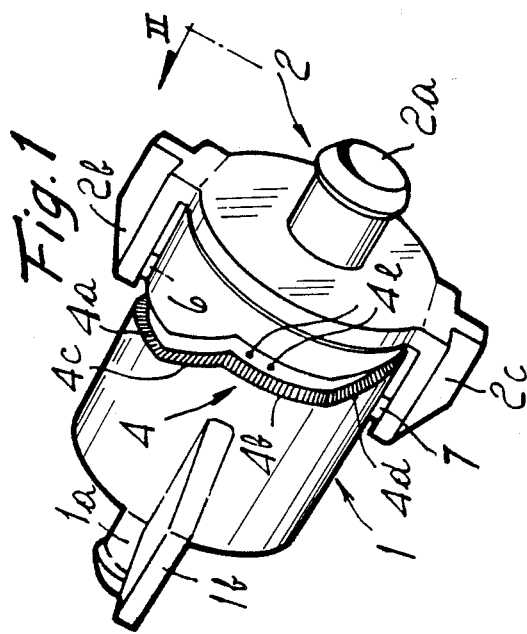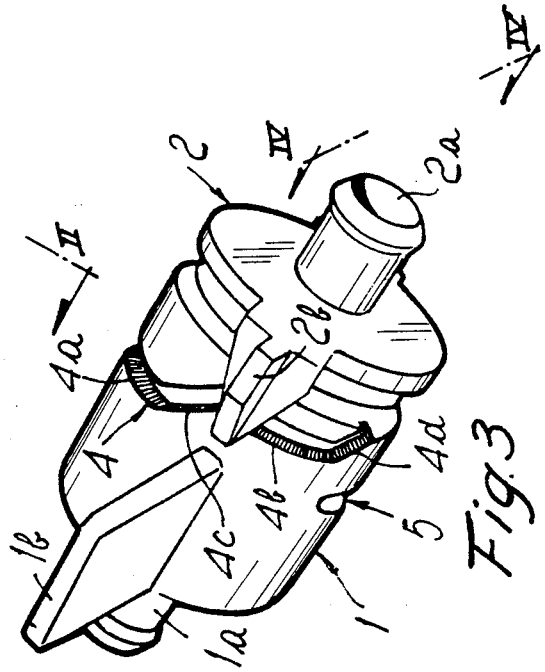

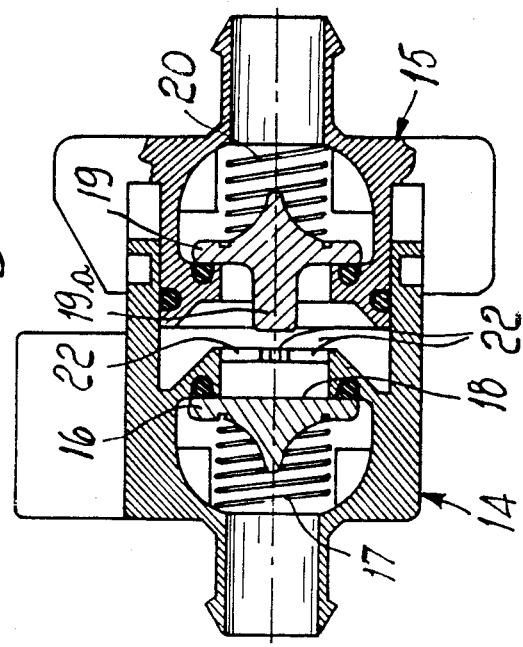
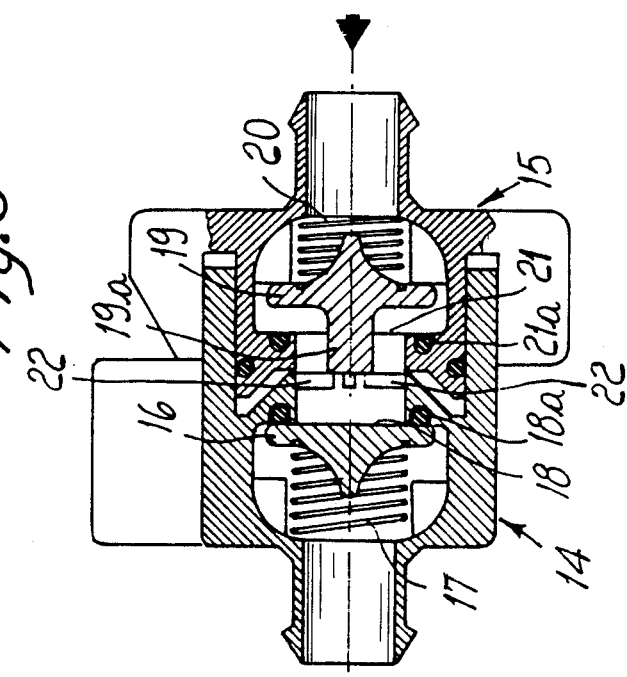

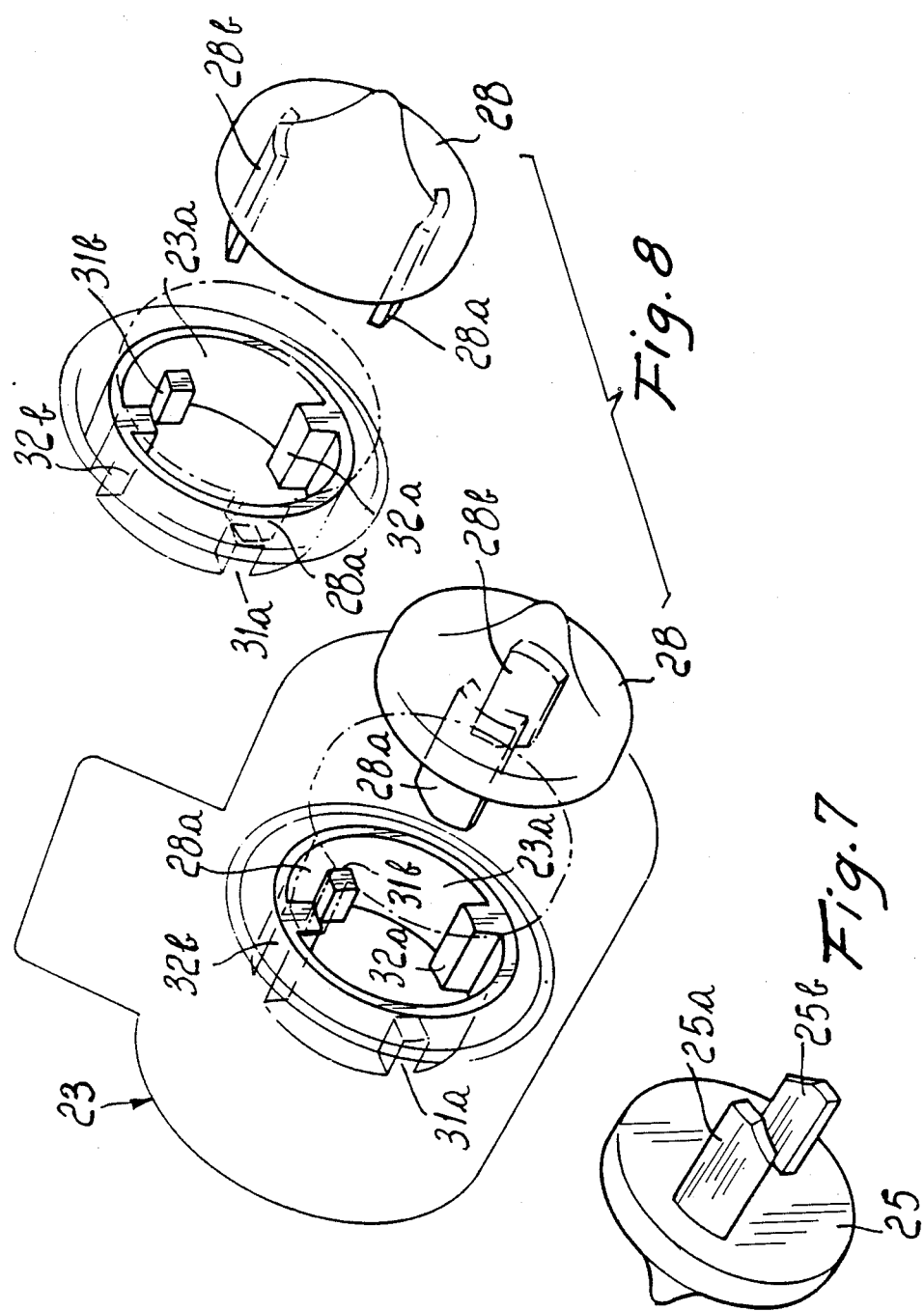

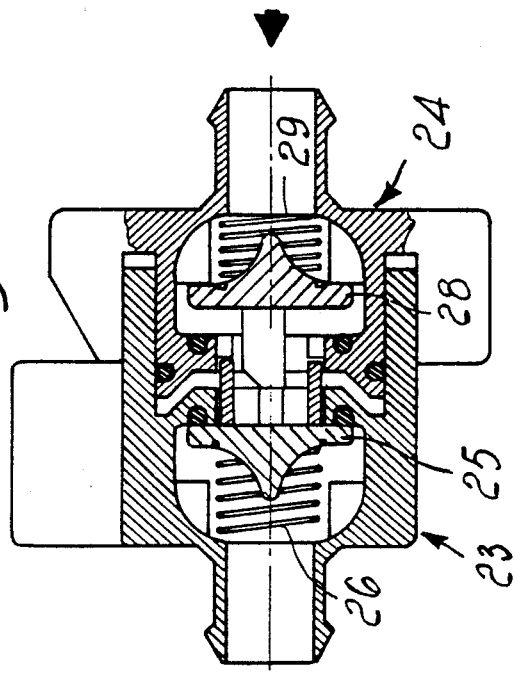
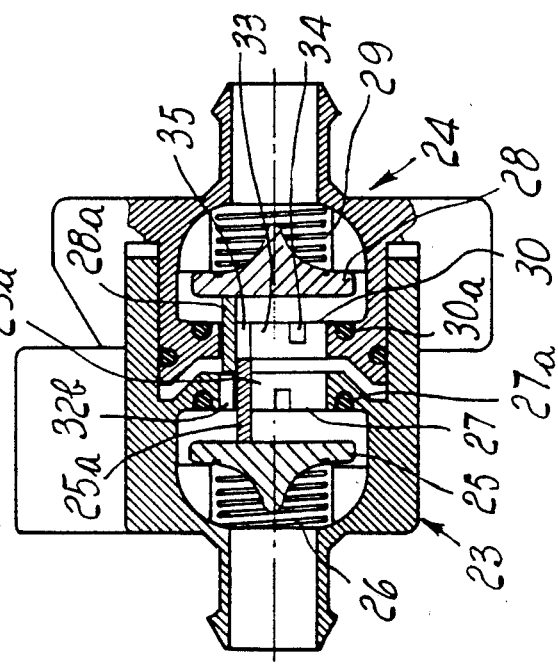

FLUID CUTOFF DEVICE IN A FLUID LINE

BACKGROUND OF THE INVENTION

The invention relates to a fluid cutoff device in a fluid line; particularly a blood carrying line in a medical device.

It is often necessary to seal off the fluid flow in a fluid carrying line; for example, that of a bypass line in a medical device. Such lines must normally be cut off to prevent the flow of blood or other fluid, temporarily, then the cutoff device must be releasable so that the fluid can once again flow through the line.

Currently such lines are sealed off by using a clamp. The clamped system has several disadvantages, namely that it is cumbersome and requires space not normally available in extracorporeal systems.

The object of the present invention is to provide a fluid cutoff device in a fluid line which has a low cost and minimum bulk, and allows the line which lead to the device to be cut off into two sealed branches, so as to control fluid flow and to allow the connection or disconnection of a component within the system.

Another object of the invention is to provide a one-way fluid flow device.

SUMMARY OF THE INVENTION

The described objects are achieved by a fluid cutoff device in a line, according to the invention includes a first coupling which has a central axis, a proximal end for connection to a fluid line, a generally cylindrically shaped outer body, and a hollow generally cylindrically shaped inner body with a first inner sealing surface. The first coupling includes a first shutter valve enclosed within the first coupling and is adapted to be normally biased closed to abut against the first sealing surface to cut off fluid flow through the first coupling. The device includes a second coupling which has a central axis, a proximal end for connection to a fluid line, a generally cylindrically shaped outer body adapted to sealably translate within the inner body of said first coupling, a hollow generally cylindrically shaped inner body with a second inner sealing surface. The second coupling includes a second shutter valve enclosed within the second coupling and is adapted to be normally biased closed against the second sealing surface to cut off fluid flow through the second coupling. The device has a first actuation means within the first coupling which is engagable with the second shutter valve and adapted to separate the second shutter valve from the second sealing surface to open the second coupling upon sufficient translational engagement of the second coupling into said first coupling; and has means for controlling the translational engagement of said couplings. The device thereby functions as a one-way valve.

The device functions as a full open flow device by including a second actuation means within the second coupling engagable with the first shutter valve and is adapted to separate the first shutter valve from the first sealing surface to open the first coupling upon sufficient translational engagement of the second coupling into the first coupling.

DETAILED DESCRIPTION OF THE INVENTION

Further characteristics and advantages of the invention will become apparent from the followed description of some preferred but not exclusive embodiments of the invention, illustrated only by way of non-limitative example in the accompany drawings, wherein:

FIG. 1 is a perspective view of the invention in the position in which the fluid flow is allowed;

FIG. 2 is a sectional view taken along the plane II—II of FIG. 1;

FIG. 3 is a perspective view of the invention in the fluid cutoff position;

FIG. 4 is a sectional view taken along the plane IV—IV of FIG. 3;

FIG. 5 is a sectional view of the invention, according to another embodiment with the device functioning additionally as a one-way valve;

FIG. 6 is a sectional view of the invention according to the embodiment of FIG. 5 in cutoff position;

FIG. 7 is a schematic view of some elements of the invention according to another embodiment;

FIG. 8 is a schematic view of the same elements of FIG. 7 with the shutter valve in a different position;

FIG. 9 is a sectional view of the invention in open position with both shutter valves arranged according to the embodiment illustrated in FIG. 7;

FIG. 10 is a sectional view of another embodiment of the invention functioning additionally as a one-way valve.

With reference to the above described FIGS. 1, 2, 3, 4, the reference numerals 1 and 2 indicate two interconnected couplings respectively provided with connectors 1a and 2a to two branches of a line and with grip elements constituted by a tab 1b and by the pair of opposed tabs 2b, 2c. The couplings are in contact at the respective cylindrical surfaces 3a, 3b (see particularly FIG. 4) and a sealing gasket, 3c, which prevents any external contact of the fluid which flows through the device, and therefore ensures the seal and sterility of the device.

The outer surface of the coupling 1 has two identical grooves in diametrically opposed positions. The groove generally indicated by the reference numeral 4 is nearly entirely visible in FIGS. 1 and 3, while the opposed groove indicated by the reference numeral 5 can be seen only at its end portion in FIG. 3. Groove 4 includes two lateral portions 4a and 4b (perpendicularly oriented and offset relative to the longitudinal axis) connected by an inclined portion 4c, and the portion 4b is connected by an inclined portion 4d which extends to the end of the coupling and is open to provide access to the groove. The groove 5 has the same, but diametrically opposed, configuration.

A follower pin 6 extends from the tab 2b of the coupling 2 and slides within the groove 4. The groove includes an obstacle constituted by small detent studs 4e which can be passed by elastic deformation of the pin and provides a slight locking action for an operator. Similarly, an opposed follower pin 7 extends from the tab 2c of the coupling 2 and slides in the groove 5.

A shutter valve 8 is arranged within the coupling 1 and is biased by a spring 9 against a sealing surface 10 and a gasket 10a provided within the coupling 1. Similarly, the coupling 2 contains a shutter valve 11, which is biased by a spring 12 against a sealing surface 13 having a gasket 13a provided within the coupling 2. The shutter valves 8, 11 respectively have facing protrusions 8a and 11a to provide the operating functions of the cutoff device.

As illustrated in FIGS. 1 and 2, the two couplings 1, 2 are in the position of maximum mutual approach, as determined by the location of the pin 6 in the lateral portion 4a of the groove 4 and of the pin 7 in the similar portion of the groove 5. In this position the two protrusions 8a and 11a are adapted to be in sufficient mutual contact, and overcome the bias forces of the springs 9 and 12, to force the respective shutter valves 8 and 11 to be well separated from contact with their respective sealing surface 10 and 13. This is therefore the open position of the device, and the fluid can flow in both directions.

By rotating the couplings 1 and 2 counter-clockwise until they move to the relatively spaced apart position of FIGS. 3 and 4, the pin 6 is within lateral portion 4b of the groove 4 and the protrusions 8a and 11a are adapted to have a slight clearance; therefore, the shutters valves 8 and 11 are pressed by the action of the springs to make contact with their respective sealing surfaces 10 and 13. This is therefore the cutoff position of the device. It should be noted that so long as the pins remain in the lateral portions (4b) of the grooves (assisted to so remain by the detent studs 4e), the couplings continue to be engaged but each of the two branches of a line is cut off by an individual shutter. The branch which reaches the coupling 1 is sealed by the shutter valve 8, and the branch which reaches the coupling 2 is sealed by the shutter valve 11.

A further counter-clockwise relative rotation of the couplings from the above described cutoff position, allows the follower pins 6 and 7 to further slide along the respective inclined portions (illustrated as 4d in FIG. 3) of grooves 5 and 6, then completely out of the open ends of the grooves to disengage the couplings and therefore to disconnect the two sealed branches of the line without fluid losses.

FIGS. 5 and 6 illustrate a second embodiment and the device is arranged to function as a one-way valve (as shown in FIG. 5), as well as a cut-off device (as shown in FIG. 6). Couplings 14 and 15 of this embodiment have an external configuration which is identical to that of the previously described couplings 1 and 2, with similar grooves for the accommodation of similar follower pins, and therefore have identical characteristics of relative motion from a position of maximum approach shown in FIG. 5 to a relatively spaced-apart position shown in FIG. 6.

The coupling 14 contains a shutter valve 16, biased by a spring 17 against a sealing surface 18 which has a gasket 18.

The coupling 15 contains a shutter valve 19 which is pushed by a spring 29 against the sealing surface 21 which has a gasket 21a. Shutter valve 19 has a protrusion 19a adapted to make contact with a baffle 22 provided within the coupling 14. Shutter valve 16 does not have a protrusion element and is not actuated by contact with the baffle 22 to open the valve. As shown in FIG. 5, the couplings are in position of maximum mutual approach. The protrusion 19a of the shutter valve 19 is in contact with the baffle 22 of the coupling 14, and therefore the shutter valve 19 is pushed against spring 20 into a position of separation from its related sealing surface 21. Flow can occur through the coupling 15 and against the inner surface of shutter valve 16. Under such fluid force and the selection of spring 17 having the appropriate resistance, the shutter valve 16 is forced to compress the spring and separate from its sealing surface 18 to function as a one-way valve. Fluid pressure in the opposite direction forces shutter valve 16 against sealing surface 18 and therefore flow in the opposite direction is impossible. As previously discussed, continued relative counter-clockwise rotation of couplings 14 and 15 (due to the follower pins in portion 4b of the grooves) results in loss of contact between the protrusion 19a of the shutter valve 19 and the baffle 22, and the spring 20, and forces shutter valve 19 against the sealing surface 21, to also seal this branch of the device.

A third embodiment of the device, is illustrated in FIGS. 7, 8, 9, 10, in which couplings 23 and 24 have an external configuration which is similar to that described in reference to couplings 1 and 2 of FIGS. 1 and 2. The couplings include similar grooves for the accommodation of similar follower pins which guide the couplings from a position of maximum mutual approach (as shown in FIGS. 9 and 10), to relatively spaced position which functions to cut off the fluid, and further to completely disconnect the couplings. The two couplings 23 and 24 contain two shutter valves 25 and 28. The shutter valve 25 is enclosed in the coupling 23, and is provided with opposite tabs 25a and 25b in the shape of portions of a cylindrical surface and is pushed by a spring 26 against a sealing surface 27 and gasket 27a within the coupling. The valve 28 is enclosed in the coupling 24, and is also provided with tabs 28a and 28b (which are outboard of tabs 25a and 25b) and is pushed by a spring 29 against a sealing surface 30 and gasket 30a within the coupling. The coupling 23 includes an internal cylindrical surface 23a which has a pair of opposed short axial ridges 31a and 31b and a pair of equally spaced opposed longer axial ridges 32a and 32b. The ridges define two distinct relationships between the couplings and the opposed shutter valves. The tabs 25a and 25b may be accommodated in the spaces respectively between the ridges 31a, 32a and 32b, 31b or in the spaces respectively between the ridges 31a, 32b and 32a, 31b.

The same relationship occurs in the coupling 24 which has an internal cylindrical surface 33 which has a pair of opposite short axial ridges 34 and a pair of opposite long axial ridges 35. Similarly, the ridges define two distinct relationships between the coupling and the shutter valve tabs 28a, 28b.

FIG. 7 and 9 illustrate (in solid lines) the shutter valve 28 in the first relationship of mutual spacing of the couplings. When the couplings approach one another, shutter valve 28 moves and rotates together with the coupling 24 due to the force exerted by the ridges of the surface 33 on the tabs, and moves to the position shown in broken and dotted lines with the tab 28a against the long ridge 32b of the cylindrical surface 23a of the coupling 23. With the tab 28b against the other long ridge 32a of the surface, thus providing the separation of the shutter valve 28 from the related sealing surface 30, as is clearly shown in FIG. 9. The shutter valve, as shown in FIG. 9, is also arranged with its tabs between the ridges of the surface 23a of the coupling 23 so as to make contact with the tabs in the relationship of maximum mutual approach of the couplings against the long ridges of the surface 33 of the coupling 24. Also, with the tab 25a against the long ridge 35, the shutter valve 25 is separated from its sealing surface 27; and therefore, the device allows the flow of the fluid in both directions and is thus in its open position.

FIG. 8 illustrates in solid lines the shutter valve 28 in its second relationship in the position of mutual spacing of the couplings. In this position, when the couplings approach, shutter valve 28 moves to the position shown in broken and dotted lines with the tab 28a at the short ridge 31a of the surface 23a of the coupling 23 and with the tab 28b at the other short ridge 31b. In this relationship, the shutter valve 28 is pressed by spring 29 against the sealing surface 30. In this configuration, the other shutter valve 25 must be caused to separate from its sealing surface in the position of maximum mutual approach of the couplings, thus providing a one-way device which allows the flow exclusively in one direction, from the coupling 23 towards the coupling 24.

If instead it is required to provide a one-way device with a single possible flow from the coupling 24 to the coupling 23, the elements of the device are arranged as illustrated in FIG. 10. The shutter valve 28 is positioned so that its tabs contact, in the position of maximum mutual approach of the coupling, with the long ridges of the coupling 23. In this position, shutter valve 28 is separated from its sealing surface, and the shutter valve 25 is positioned with its tabs facing the short ridges of the coupling 24, against its sealing surface but which can be separated by fluid pressure on the inner surface of shutter valve 25.

The described invention is susceptible to numerous modifications and variations, all within the scope of the inventive concept: thus, for example, the cam action provided by the grooves on the outer surface of the couplings may differ in shape from the one described. In the practical embodiments of the invention, all the details may be replaced with other equivalent elements:

I claim:

1. A device for the connection, or cutoff, or sealed separation of two branches of a fluid line, comprising:
    a first coupling having a central axis, a proximal end for connection to a fluid line, a generally cylindrically shaped outer body, and a hollow generally cylindrically shaped inner body with a first inner sealing surface;
    a first shutter valve enclosed within said first coupling and adapted to be normally biased closed to abut against the first sealing surface to cut off fluid flow through the first coupling;
    a second coupling having a central axis, a proximal end for connection to a fluid line, a generally cylindrically shaped outer body adapted to sealably translate within the inner body of said first coupling, a hollow generally cylindrically shaped inner body with a second inner sealing surface;
    a second shutter valve enclosed within said second coupling and adapted to be normally biased closed against the second sealing surface to cut off fluid flow through the second coupling;
    a first actuation means within said first coupling engagable with said second shutter valve and adapted to separate said second shutter valve from the second sealing surface to open said second coupling upon sufficient translational engagement of said second coupling into said first coupling;
    said first coupling having a groove in the outer body thereof which has an open distal end, and which extends from the open end thereof along a first longitudinally spiralled portion to a first lateral portion which is perpendicular to the axis of the device, then further along a second longitudinally spiralled portion to a second lateral portion which is perpendicular to the axis of the device;
    said second coupling having a follower pin which extends from the proximal end thereof and is adapted to slide along the groove in said first coupling, whereby the engagement of the follower pin in the first lateral portion corresponds to a spaced apart relationship of said first and second couplings so that said first and second shutter valves are closed, and the engagement of the follower pin in the second lateral portion corresponds to a maximum mutual engagement of said first and second couplings to open at least one of said shutter valves.

2. A device as in claim 1 further comprising a second actuation means within said second coupling engagable with said first shutter valve and adapted to separate said first shutter valve from the first sealing surface to open said first coupling upon sufficient translational engagement of said second coupling into said first coupling.

3. A device as in claim 2, wherein:
    said first actuation means comprises a first protrusion which extends from the distal end of said first shutter valve;
    said second actuation means comprises a second protrusion which extends from the distal end of said second shutter valve; and
    said first and second protrusions are adapted to abut each other upon sufficient translational engagement of said couplings to open said first and second shutter valves for allowing fluid to flow through the device.

4. A device as in claim 2 wherein said first actuation means comprises a first axial ridge arranged upon the inner body of said first coupling;
    and said second actuation means comprises a second axial ridge arranged upon the inner body of said second coupling;
    wherein said first shutter valve further includes a tab extended axially therefrom and adapted to engage said second axial ridge upon sufficient translational engagement of said couplings, and
    wherein said second shutter valve further includes a tab extended axially therefrom and adopted to engage said first axial ridge upon sufficient translational engagement of said couplings.

5. A device as in claim 2 wherein:
    the inner body of said first coupling further has a first pair of opposed short axial ridges, and has an equally spaced first pair of opposed long axial ridges;
    The inner body of said second coupling further has a second pair of opposed short axial ridges, and has an equally spaced second pair of opposed long axial ridges;
    said first shutter valve includes a first pair of opposed tabs extending axially therefrom and adapted to engage one of said second pair of short axial ridges and said second pair of long axial ridges upon sufficient translational engagement of said couplings; and
    said second shutter valve includes a second pair of opposed tabs extending axially therefrom and adapted to engage one of said first pair of axial short ridges and said first pair of long axial ridges upon sufficient translational engagement of said couplings,
    whereby when said first pair of tabs are arranged to engage said second pair of short axial ridges, said first shutter valve is against the first sealing surface; and when said first pair of tabs are arranged to engage said second pair of long axial ridges, said first shutter valve is separated from the first sealing surface; and and whereby when said second pair of tabs are arranged to engage said first pair of short axial ridges, said second shutter valve is against the second sealing surface; and when said second pair of tabs are arranged to engage said first pair of long axial ridges, said second shutter valve is separated from the second sealing surface.

6. A device as in claim 1 wherein said second shutter valve includes a second protrusion which extends from the distal end thereof, and wherein said first actuation means comprises a baffle within the inner body of said first coupling, which is adapted to abut said second protrusion upon sufficient translational engagement of said couplings.

7. A device as in claim 1 wherein said first coupling further comprises a second groove having the same but diametrically opposed configuration, and said second coupling having a second follower pin adapted to slide along said second groove.

8. A device as in claim 1 wherein the first lateral portion further includes at least one small stud for providing elastic resistance with said follower pin to facilitate retention of the follower pin in the first lateral portion.

* * * * *